United States Patent [19]

Watkins et al.

[11] 3,995,617
[45] Dec. 7, 1976

[54] HEART ASSIST METHOD AND CATHETER

[76] Inventors: David H. Watkins, 6039 N. Waterbury Road, Des Moines, Iowa 50312; Erwin J. Klink, 814 Laurel Circle SE., Albuquerque, N. Mex. 87108

[22] Filed: May 31, 1972

[21] Appl. No.: 258,272

[52] U.S. Cl. .............................. 128/1 D; 128/348
[51] Int. Cl.² ........................................ A61M 1/03
[58] Field of Search ............. 128/1 D, 214 R, 274, 128/348; 417/387, 478–479, 566

[56] References Cited
UNITED STATES PATENTS

| | | | |
|---|---|---|---|
| 3,384,089 | 5/1968 | Shriner | 128/350 R |
| 3,568,659 | 3/1971 | Karnegis | 128/1 D |
| 3,592,184 | 7/1971 | Watkins et al. | 128/1 D |

OTHER PUBLICATIONS

Schuhmann et al.,–*Surgery*, vol. 67, No. 6, June 1970, pp. 957–968.
Stanley–*Surgery*–Apr. 1969, vol. 65, No. 4, pp. 649–658.
Sirak et al.–*Surgery*, vol. 28, No. 2, 1950, pp. 225–234.

*Primary Examiner*—Dalton L. Truluck

[57] ABSTRACT

Method and device for augmenting the action of an ailing heart having an incompetent aortic valve or incompetent left ventricle wherein blood is directly sucked from the left ventricle, while blocking flow to the aorta, and then upon reverse cycle, the blood removed is forced into the aorta, while blocking flow back into the left ventricle.

9 Claims, 6 Drawing Figures

HEART ASSIST METHOD AND CATHETER

As a matter of introduction, our invention relates to method and apparatus for augmenting the action of the ailing heart.

Among the objects of the invention is the provision of a method and device for effectively moving blood from the left ventricle of the heart in safe, effective and reliable manner, and then discharging the said blood into the aorta.

Other objects of our invention in part will be apparent and in part particularly pointed to in the description which follows.

The invention, then, may be considered to reside in the several operational steps and the relation of each of the same to one or more of the others, as well as in the combination of elements, features of construction and arrangement of parts, all as described herein and set out in the claims at the end of this specification.

CROSS-REFERENCE TO RELATED APPLICATIONS

The present application for patent is generally related to our U.S. Pat. Nos. 3,592,183 and 3,592,184, both issued July 13, 1971, and titled respectively, "Heart Assist Method and Apparatus" and "Heart Assist Method and Catheter."

BACKGROUND OF THE INVENTION

As an aid to a better understanding of certain features of our invention, it may be noted that situations occur where the normal heart action of the patient is insufficient to supply the patient's bodily needs. As an example, during operative or post-operative periods, which may last for as much as some 5 or 6 hours, there well may be a lack of sufficient muscular activity within the heart itself to supply sufficient blood. This may derive from trauma, ischemic shock or postoperative shock. Or it may derive from a general overall deteriorating condition of the patient.

It is our view that the substantial decrease in heart activity, or even a virtual loss of such activity, derives from an incompetent or diseased left ventricle of the heart. Actually, it is our thought that, in many instances, the action of the left ventricle is wholly insufficient to completely discharge its contents. Pump failure of the heart is the basic physiologic defect of the diseased heart affected by severe myocardial infarction due to coronary artery disease.

Although many efforts have been made in the past to overcome the deficiencies of an ailing heart, we find that, for one reason or another, these efforts have not been entirely satisfactory. In some instances, the apparatus involved have been too expensive or too complicated. And, in others, they are found to be insufficiently reliable.

An object of our invention, therefore, is to provide a method and device for overcoming the deficiencies of the prior art, and assure effective movement of blood from the incompetent heart, and discharge the same into the aorta, and thence into the arterial tree in safe, reliable and efficient manner.

SUMMARY OF THE INVENTION

Turning now to the practice of our invention, we provide a method and device for aiding the action of an ailing heart, particularly the unavailing or subcritically diminished contractility of the left ventricle because of massive destruction or adynamia produced by myocardial infarction or other process, such as hemorrhagic shock. Our catheter of novel construction is introduced into the aorta by way of an incision in the subclavian artery or other suitable vessel, with proximate end protruding from the artery and distal end extending well into the left ventricle.

The proximate end of the catheter is provided with a plastic tube connecting to a reciprocating pump and apparatus of the character more particularly described in our U.S. Pat. No. 3,592,183, more fully identified above. The distal end, placed well into the cavity of the left ventricle, is provided with an opening or aperture with internallylocated valve means effecting a closure of the opening upon a pressure being established within the catheter and, with a suction being established, assuring a free passage through the opening. Well back of the distal end of the catheter, there are provided a multiplicity of openings in the wall thereof, with exteriorly-located valve means to close off the openings when suction is established within the catheter and, upon pressure being established, freely open the same.

The construction of our device is such that during normal systolic period of the heart, and a suction action being had by reason of the timed action of the reciprocating pump, blood is withdrawn from the cavity of the left ventricle. And during ventricular diastole, and a pressure being established by the pump, this same blood is reintroduced into the aorta. The removal of blood from the left ventricle is direct and depends only upon filling of the left ventricular cavity from the left atrium and not upon the injection of blood into the root of the aorta by contraction of the left ventricle and its attendant myocardium.

As a further feature, we conveniently supply our catheter with two pressure-detecting channels along the wall thereof, with appropriate pressure gauge, one channel leading to the distal end of the catheter and measuring the left intraventricular pressure, and the other leading to the mulitplicity of openings back from the aortic valve and measuring the aortic root pressure. By carefully observing the pressure trace patterns as the catherter is introduced, the desired location is had, that is, with distal end and opening therein with internally-located valve means well within the ventricular cavity, and the mulitplicity of openings and associated externally-located valve means back from the aortic valve and at the root of the aorta.

BRIEF DESCRIPTION OF THE DRAWINGS

We disclose in the accompanying drawings an illustrative embodiment of the device in accordance with the teachings of our invention, in which.

Like reference characters denote like parts throughout the several views of the drawings.

DESCRIPTION OF THE PREFERRED EMBODIMENTS

Figure 1:
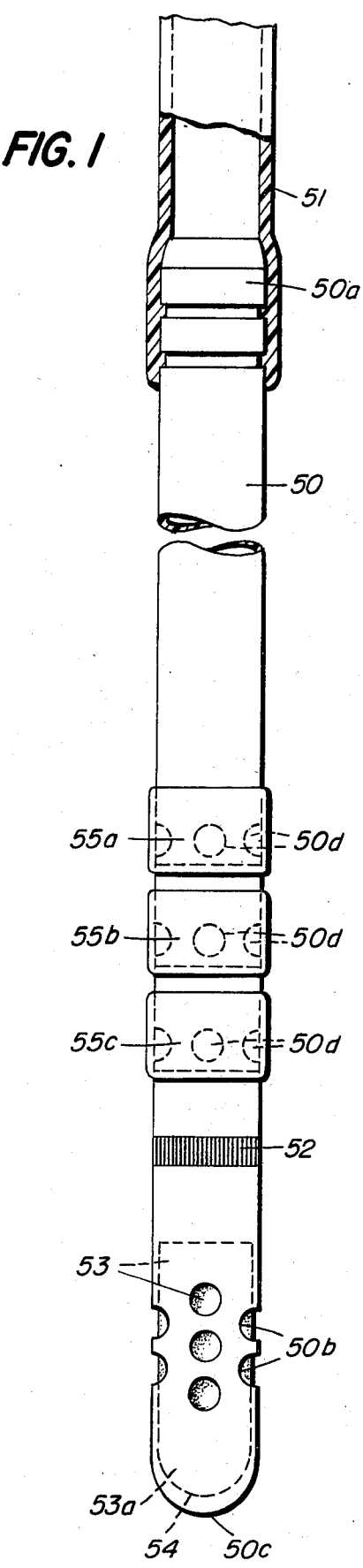
FIG. 1 is the catheter of our invention.

One form of our invention is disclosed in the FIGS. 1, 2, 3 and 4 of the drawings. It is seen that the catheter of our invention (FIG. 1) essentially comprises a hollow shaft portion 50 with proximate end 50a secured within a flexible tube 51 directly communicating with a suitable reciprocating blood pump (not shown). Now, the distal end of the catheter (see also FIG. 2) is provided with a suitable opening or aperutre 50b, just back from the tip portion 50c. Actually, the opening 50b preferably is in the form of a multiplicity of apertures in uniform spacing circumferentially about the catheter. And for best combination of results, these apertures are evenly spaced one from another.

Well back of the distal end of the catheter, there are provided a multiplicity of openings or apertures 50d. These are in the form of a multiplicity of uniformly spaced openings which preferably are arrayed in a series of rings, uniformly spaced one with regard to the other, also as illustrated in FIG. 1 of the drawings. The location of the second group of openings 50d is such with regard to the distal opening or openings 50b (see FIG. 2) that the openings 50d lie entirely within the aorta at the root of the aortic valve when the latter opening or openings 50b at the distal end of the catheter are positioned well within the ventricular cavity. The multiplicity of openings assure a free, unimpeded flow of blood into and out of the catheter openings, even though one or more may be blocked by contact with the walls of the ventricular cavity or the aortic valve, or even the walls of the aorta. And the uniform array of openings effects a balanced flow irrespective of which openings may be blocked.

As an aid to positioning the catheter, a radio-opaque marker 52 (FIG.1), such as a bit of lead, is located within the catheter wall intermediate openings 50b and 50d.

Associated with the distal opening or openings 50b is valve means 53 in the form of a rubber boot or flexible plastic boot located within the catheter shaft portion and fitting against the inner wall thereof and around the pressure channel 56. Conveniently, the boot is in the form of a thimble, with end 53a bonded to the inside of catheter tip 50c, as at 54. The construction is such that upon a suction being established within catheter 50, this by reason of the action of the reciprocating blood pump, the valve means 53 contract inwardly, as seen in FIG. 3, and readily assure a flow of blood from the ventricular cavity into the catheter passage by way of apertures 50b and along the walls of boot 53. Upon reversal of the pump, the pressure building up in the catheter closes the valve means, that is, forces the flexible boot against the openings and closes the same to effectively prevent the passage of blood back into the ventricular cavity, as seen in FIGS. 1 and 2.

Figure 2:
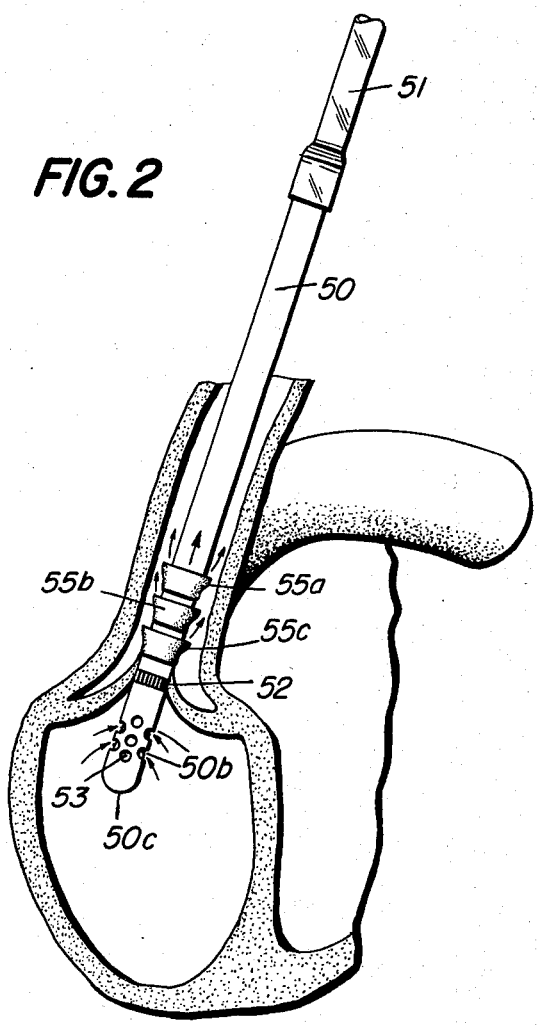
FIG. 2 is a sectional view, on reduced scale, of the catheter of FIG. 1 as introduced through the subclavian artery of a patient and positioned with distal end well into the ventricular cavity.
Figure 3:
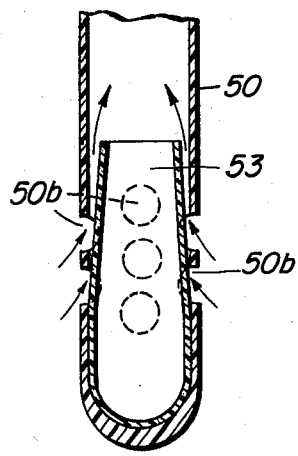
FIGS. 3 and 4(a) and 4(b) are detached views of two portions of the catheter of FIG. 1 in order to better illustrate certain features of the invention, the FIG. 3 illustrating valve and openings at the distal end and the FIGS. 4(a) and 4(b) the valve and openings back therefrom respectively in closed and open positions.
Figure 4A:
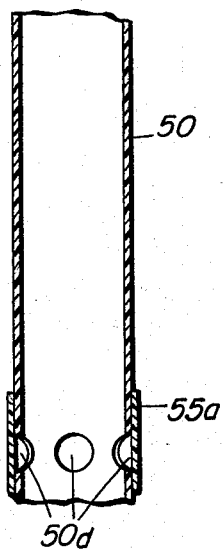
Figure 4B:
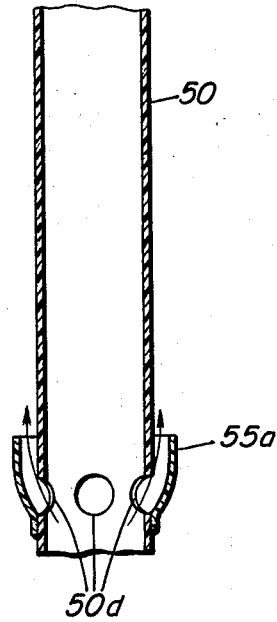

The multiplicity of openings 50d back from the distal end of the catheter, conveniently in the form of a plurality of rings (three are shown in FIGS. 1 and 2), are provided with a corresponding plurality of externally located rubber or flexible plastic cylinders or boots (55a, 55b and 55c), appropriately bonded to the outside wall of the catheter. And with suction being established within catheter 50, and blood from the ventricular cavity entering openings 50b, any flow outwardly into the aorta by way of openings 50d is effectively prevented by closing of the cylinders or boots 55a, 55b, and 55c against the outside wall of the catheter as seen in FIG. 4(a). But with reversal of reciprocating pump and the establishment of a pressure within the catheter, the blood withdrawn from the ventricular cavity is forced out through openings 50d, this with consequent expansion of boots 55a, 55b and 55c, as more particularly indicated in FIG. 4(b), and into the aorta and, thence, to the arterial tree.

The construction is such that the entire diastolic filling volume of the left ventricle, this corresponding to an ideal stroke volume, is withdrawn from the left ventricular cavity and then reinjected into the proximal aorta, just distal to the aortic valve. Our catheter obviates the requirement for ventricular systole and depends entirely upon the venous return blood flow from the lungs. The construction is particularly suited to those patients having an incompetent aortic valve or subcritically diminished contractility of the left ventricle because of some destruction of the same as a result of hemorrhagic shock or the like.

Figure 5:
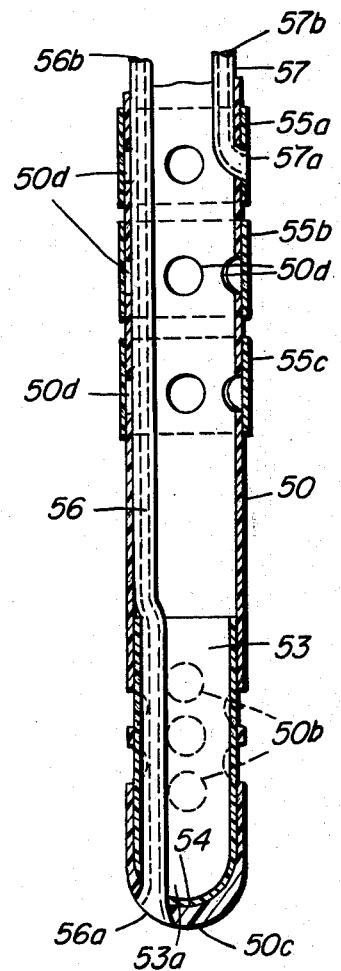
FIG. 5 is a sectional view of a modified catheter according to our invention, showing pressure-detecting channels used primarily for measuring ventricular cavity and aortic root pressures.

As a further embodiment of the construction of our catheter, this with regard to the means and manner for placing the same properly within the aorta, with distal end of the catheter well within the ventricular cavity, we provide two pressure-detecting channels. The shaft portion 50 of our catheter (see FIG. 5) is supplied with an interior channel member 56 secured to the inner wall thereof, with distal end 56a positioned at the distal end of the catheter. A suitable gauge connecting through a two-way valve (not shown) communicates with the proximate end 56b of channel 56, for effectively measuring the pressure obtained at opening or aperture 56a. The two-way valve allows cahnnel 56 to be switched from the pressure measuring gauge to providing a simple and convenient means for injecting medications directly into the ventricle cavity, for obtaining blood samples from the ventricle cavity, or for introducing means for detecting an intraventricular electrocardiogram. An easy route of access to the ventricular cavity is provided for these and diverse other applications.

A corresponding channel member 57, similarly secured to the inner wall of catheter 50 is provided with open end portion 57a communicating with the outside of the catheter. A suitable gauge connected through a two-way valve (not shown) connecting with the proximate end 57b of the channel effectively measures pressures obtaining in opening or aperture 57a positioned at the root of the aorta. The two-way valve allows channel 57 to be switched from the pressure measuring gauge to providing a simple and convenient means for obtaining blood samples from the root of the aorta or for introducing sensing devices to measure features of blood flow, such as velocity and acceleration measuring devices, and, by this easy route of access, for diverse other applications. By noting the pressure readings of the two gauges and the changes in these pressures as the catheter is introduced into the aorta through the aortic valve and into the ventricular cavity, proper and exact positioning is effected. Moreover, with the modified catheter construction, the pressure obtaining at the two locations, that is, within the ventricular cavity and at the root of the aorta, may be directly measured. This provides a means of determining the response of the heart to the treatment to which the patient is being subjected. In taking readings the pump may be operating or may be temporarily disconnected. If disconnected, the response of the heart free of any pump action can be determined. If the pump is operating, the response of the heart and the assistance provided by the pump can be determined.

It will be seen that we provide in our invention a catheter of simple, inexpensive and practical construction, in which the various objects herein before set forth are effectively achieved. Also, that we provide a method by which an ailing heart, with incompetent aortic valve or other inadequacies by reason of which the left intra-ventricular pressure is below a critical minimum value, is sufficiently aided to supply the needs of the body during periods of the terminal states of hypoperfusion syndromes.

Inasmuch as a number of embodiments may be made of our invention, and since various changes may be made in the embodiments set forth, it is to be understood that all matter described herein or shown in the acompanying drawings is to be interpreted as illustrative, and not by way of limitation.

We claim as our invention:

1. Method for augmenting the action of an ailing heart having a left ventricle and associated aorta wherein an open-ended catheter, with further opening back from said open end, is inserted into the aorta with open end within the left ventricle and said further opening outside of the same, comprising in sequential operation sucking blood from said left ventricle by way of the open end of said catheter during systolic pulsation, while blocking a back-flow of blood from said associated aorta; and during reverse cycle, or diastolic pulsation, forcing blood back through said catheter and into the aorta by way of said further opening while blocking a flow back into the said left ventricle.

2. A heart assist device for pumping blood directly from the left ventricle into the aorta past the aortic valve comprising catheter means including an elongated member with an axial bore therein and having a distal end for insertion into the left ventricle, said distal end having a tip portion, said tip portion having therein an opening in fluid communication with said bore, said distal end also being provided with a second set of openings axially spaced from said tip opening, said second set of openings also communicating with said bore, first check valve means associated with said tip opening and closing same during first predetermined intervals and opening same during second predetermined intervals and second check valve means associated with said second set of openings and closing said second set of openings during said second predetermined intervals and opening same during said first predetermined intervals.

3. A heart assist device for pumping blood directly from the left ventricle into the aorta past the aortic valve comprising catheter means including an elongated member with an axial bore therein and having a distal end for insertion into the left ventricle, said distal end having a tip portion, said tip portion having therein an opening in fluid communication with said bore, said distal end also being provided with a second set of openings axially spaced from said tip opening, said second set of openings also communicating with said bore, first check valve means interiorly located against said tip opening and closing same upon a pressure being established in said catheter bore and opening same upon suction being established therein, and second check valve means exteriorly located about said second set of openings and closing said second set of openings upon suction being established in said catheter bore and opening same upon pressure being established therein.

4. A method for augmenting the action of an ailing heart having a left ventricle and associated aorta comprising inserting a catheter tip having spaced apart inlet and outlet check valves thereon into the aorta, through the aortic valve and into the left ventricle, said inlet check valve being located adjacent the tip end of the catheter so that blood may be sucked into the catheter from the left ventricle, said outlet check valve being proximally spaced from the tip end of the catheter so as to be located outside the aortic valve permitting blood within the catheter to be pumped directly into the aorta and sequentially sucking blood from said left ventricle by way of said inlet valve of the catheter during systolic pulsation and on reverse cycle, forcing all of said sucked blood back through the catheter and into said aorta via said outlet check valve.

5. Heart assist device comprising catheter means including an elongated portion with axial bore therein and having a distal end with opening therein letting into said bore and a mulitplicity of further openings axially spaced back from said first-mentioned opening and also letting into said bore; first valve means exteriorly located about said multiplicity of further openings and closing said further openings upon suction being established in said catheter and opening said further openings upon pressure being established therein; and second valve means interiorly located against said first-mentioned opening and closing the same upon a pressure being established in said catheter and opening the same upon suction being established therein.

6. Device acording to claim 5, wherein said first valve means is in the form of a flexible boot positioned externally on said catheter bore and secured thereto; and said second valve means is in the form of a further flexible boot positioned interiorly of said catheter bore and secured thereto.

7. Device according to claim 5, wherein said distal end opening is in the form of a multiplicity of uniformly-spaced individual openings, and said multiplicity of further openings is in the form of a ring of uniformly-spaced individual openings.

8. Device according to claim 5, wherein the elongated portion of said catheter is fashioned of plastic and wherein an opaque marker is positioned within the wall thereof at a point between said first opening and said multiplicity of further openings.

9. Device according to claim 5, wherein channel means are provided in said catheter communicating with said opening in the distal end thereof to permit measurement of left intraventricular pressure and further channel means are provided in said catheter communicating with said further openings to permit measurement of aortic root pressure.

* * * * *